United States Patent [19]

Zare et al.

[11] Patent Number: 5,009,760

[45] Date of Patent: Apr. 23, 1991

[54] SYSTEM FOR MEASURING ELECTROKINETIC PROPERTIES AND FOR CHARACTERIZING ELECTROKINETIC SEPARATIONS BY MONITORING CURRENT IN ELECTROPHORESIS

[75] Inventors: Richard N. Zare, Stanford; Xiaohua Huang, Mountain View; Jack I. Ohms, Palo Alto, all of Calif.

[73] Assignee: Board of Trustees of the Leland Stanford Junior University, Stanford, Calif.

[21] Appl. No.: 456,594

[22] Filed: Dec. 29, 1989

Related U.S. Application Data

[63] Continuation-in-part of Ser. No. 386,991, Jul. 28, 1989, abandoned.

[51] Int. Cl.$^5$ ................. G01N 27/26; B01D 57/02
[52] U.S. Cl. .................... 204/183.3; 244/180.1; 244/299 R
[58] Field of Search .............. 204/299 R, 180.1, 183.3

[56] References Cited

PUBLICATIONS

Zare, R. N. et al., "Current-Monitoring Method for Measuring the Electroosmotic Flow Rate in Capillary Zone Electrophoresis", *Analytical Chemistry*, 60 (1988), 1837–1838.

*Primary Examiner*—John F. Niebling
*Assistant Examiner*—John S. Starsiak, Jr.

*Attorney, Agent, or Firm*—Majestic, Parsons, Siebert & Hsue

[57] ABSTRACT

The electroosmotic velocity of an electrolyte is determined by displacing the electrolyte which fills a capillary tube by a second electrolyte which has the same composition as the first electrolyte but of a different concentration. The current flowing through the electrolyte is monitored until the current value becomes constant, indicating that all of the first electrolyte has been replaced by the second electrolyte. The time required for the first electrolyte to be entirely replaced by the second electrolyte is therefore measured to yield the electroosmotic velocity. Any components of samples in the electrolyte can also be detected by a detector to measure its actual velocity. Such actual velocity and the electroosmotic velocity of the electrolyte as a whole enables the electrophoretic mobility of the sample component to be determined. This method also enables the measurement of migration rates of micelles. If the constant current flowing when only the second electrolyte is in the tube is measured when the same voltage is applied as an additional data point, one need not wait until all of the first electrolyte has been replaced by the second electrolyte. The current value of only a short time interval needs to be monitored. The straight line curve plotted for such short time interval can be simply extended until the current value falls or rises to the constant current value when the tube is filled by the second electrolyte to find the time needed for the first electrolyte to be entirely replaced by the second electrolyte.

13 Claims, 2 Drawing Sheets

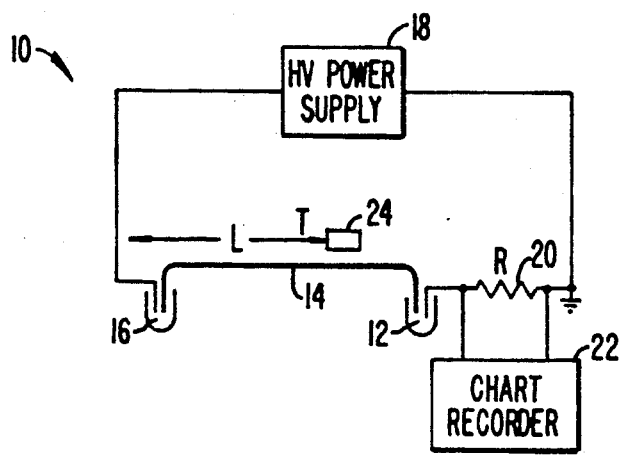
FIG._1.
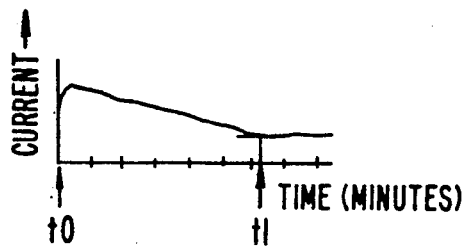
FIG._2A.
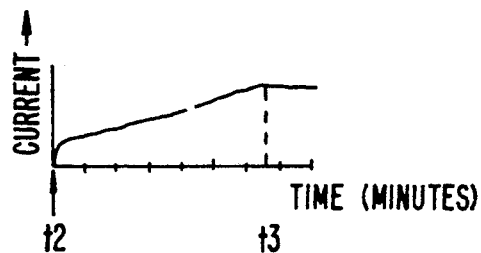
FIG._2B.
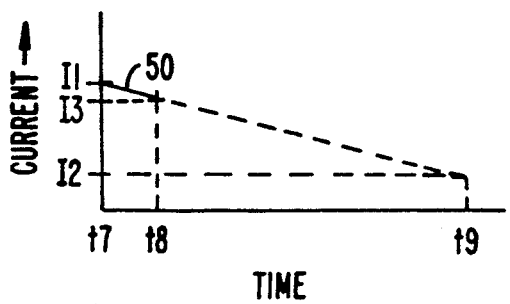
FIG._4.
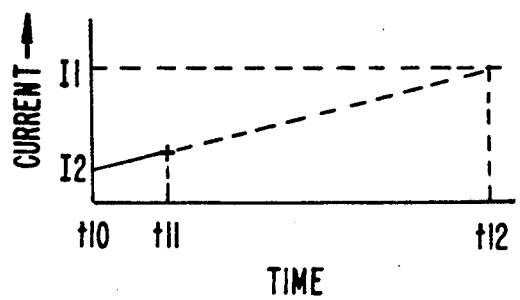
FIG._5.

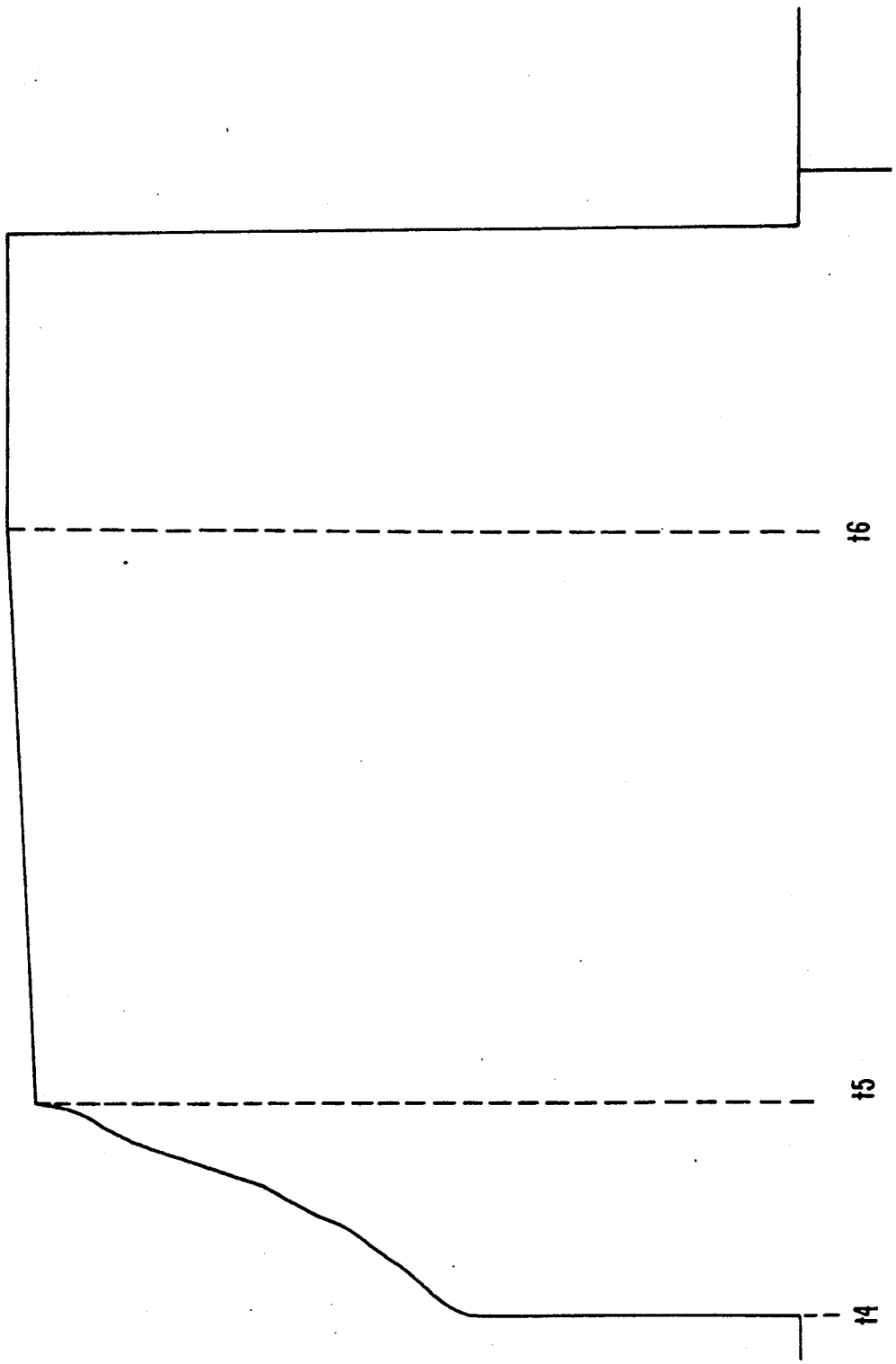
FIG._3.

5,009,760

SYSTEM FOR MEASURING ELECTROKINETIC PROPERTIES AND FOR CHARACTERIZING ELECTROKINETIC SEPARATIONS BY MONITORING CURRENT IN ELECTROPHORESIS

This is a continuation of application Ser. No. 386,991, filed July 28, 1989 now abandoned.

BACKGROUND OF THE INVENTION

This invention relates in general to capillary electrokinetic devices and in particular to an improved system for measuring electrokinetic properties and for characterizing electrokinetic separation by monitoring current in an electrophoretic process.

In capillary zone electrophoresis (CZE) a migration channel of capillary dimensions is filled with electrolyte. A sample to be analyzed is injected at one end of the channel and a high voltage is applied across the channel, causing the sample in the electrolyte to migrate from one end of the channel to the other. When the electrolyte contacts the walls of the capillary, the inner surface of the capillary becomes charged, either through ionization of surface groups on the capillary walls or through the adsorption of charged species from the electrolyte onto the inner surface. In either case the electrolyte inside the capillary is no longer electro-neutral but acquires a net charge which may be positive or negative. Under the action of the applied electric field, the electrolyte moves towards one end of the capillary, and this movement is referred to as electroosmotic (electroendosmotic) flow.

While the electrolyte as a whole acquires a net charge so that the electrolyte as a whole flows toward one end of the capillary, different components of the sample may be positively or negatively charged.

Therefore in addition to the electroosmotic flow of the electrolyte, electrophoresis also takes place; that is, the applied electric field exerts a force on positively charged species to cause them to move to the negatively charged electrode and on negatively charged species to cause them to move to the positively charged electrode. As a result, the components in the injected sample separate into distinct zones, based on their different mobilities. Frequently, the rate of electrophoretic flow is less than the rate of electroosmotic flow. Consequently, species in the injected sample move in one direction—the direction of the electroosmotic flow—and thus the different species can be detected as each zone passes through some suitable detector located downstream from the capillary inlet.

Clearly, a precise characterization of the electroosmotic flow is highly desirable not only for understanding CZE but also for optimizing the operation of CZE in analyzing a given sample. One way to measure the electroosmotic velocity is to record the migration time of an injected uncharged marker solute, which will be carried through the capillary under the action of only electroosmotic flow. This technique is described in "Capillary Zone Electrophoresis of Neutral Organic Molecules by Solvophobic Association with Tetraalkylammonium Ion" by Walbroehl and Jorgenson, ANAL. CHEM. 1986, 58, 479–481. See also ((References 1 and 2)). First, it is very difficult to select a marker which is truly neutral. Furthermore, the charge on a particular marker selected would depend upon the medium in which is it placed. Therefore, an apparently "neutral" marker used in one medium may be unsuitable for use as a marker in the different medium. In addition, "neutral" markers may be difficult to detect.

Another method for measuring electroosmotic velocities is to weigh the mass of electrolyte transferred from the capillary inlet to capillary outlet over a timed interval. For a description of the method, see "Measurement of Electroendosmotic Flows in High-Voltage Capillary Zone Electrophoresis" by Altria and Simpson, ANAL. PROC. 1986, 23, 453–454. In this method, losses caused by evaporation must be eliminated by covering the surface of the liquid in the cathode compartment with a film of silicone fluid or by use of a tight-fitting lid. Since the mass of electrolyte transferred is minute, the use of a digital balance appears to be necessary. This method requires the measurement of minute mass transfers so that extra precautions must be taken to assure the accuracy of measurement so that it is inconvenient and cumbersome to use.

None of the above described method is entirely satisfactory. It is therefore desirable to provide an improved system for measuring electrokinetic properties of a solute in which the above described difficulties are alleviated.

SUMMARY OF THE INVENTION

The apparatus of this invention is for determining the electrokinetic properties of a first electrolyte in an electrokinetic separation. The apparatus comprises an elongated capillary tube having an inlet end and an outlet end suitable for holding electrolytes and a second electrolyte suitable to be introduced into the capillary tube at the inlet end after the first electrolyte has been introduced. The second electrolyte has an electrical resistivity that differs from that of the first electrolyte but has substantially the same chemical properties as the first electrolyte. The apparatus also includes means for applying a voltage to and current through the electrolytes to cause the electroosmotic flow of the electrolytes towards the outlet end and to cause the second electrolyte to replace the first electrolyte in the tube continuously. The apparatus further includes means for measuring the current through the electrolytes in the capillary tube as a function of time. The electroosmotic velocity of the first electrolyte is determined from the current measurement as a function of time.

In one embodiment, the first electrolyte (electrolyte 1) comprises a first solution composed of a buffer and the second electrolyte (electrolyte 2) comprises a second solution of the same buffer but at a concentration different from that of the first solution. The capillary tube is filled initially with electrolyte 1 and then electrolyte 2 is continuously injected so that it replaces in a continuous manner the first electrolyte. By measuring the current change across the capillary tube as a function of time the electroosmotic velocity is determined. In this procedure, it is assumed that electrolyte 1 and electrolyte 2 have slightly different resistances but essentially the same electroosmotic velocities.

Once the electroosmotic velocity has been established, the electrophoretic mobilities of components in a sample may be determined as follows. First, the capillary tube is filled with electrolyte 1. Then a thin zone of sample is injected at the inlet to the capillary tube. Then electrolyte is electrokinetically injected. It is assumed that the presence of the components in the sample solution do not after significantly the electroosmotic velocity of electrolyte 1. By using the knowledge of the electroosmotic velocity of electrolyte and by measuring the migration times of the components in the sample solution to travel a known distance from the inlet of the capillary tube to the detector region of the capillary tube, the electrophoretic velocities of the components may be determined. With a further knowledge of the electric field strength inside the capillary tube (usually given by the ratio of the voltage applied across the tube to the length of the tube), the electrophoretic mobilities of the different components may be derived from the electrophoretic velocities.

In a second embodiment, which we regard to be the preferred embodiment, the electroosmotic velocity of the electrolyte and the electrophoretic velocities of the components in a sample solution are measured in the same experiment. This is accomplished as follows: The capillary tube is filled initially with electrolyte 1. Then a thin zone of sample solution is injected at the inlet of the capillary tube. Then electrolyte 2 is electrokinetically injected into the inlet end of the capillary tube so that it replaces electrolyte 1. By measuring the current change across the capillary as a function of time as well as measuring the migration times of the different components in the sample solution to travel a known distance from the inlet end to the detected region of the capillary, it is possible to determine the electroosmotic velocities of the electrolyte as well as the electrophoretic velocities of the individual sample components. The electrophoretic mobilities of the components can then be determined from the electric field strength in the tube and the electrophoretic velocities as before in the first embodiment.

BRIEF DESCRIPTION OF THE DRAWINGS

FIG. 1 is a schematic diagram of an electrokinetic system for measuring the electroosmotic velocity to illustrate the preferred embodiment of the invention.

FIGS. 2A, 2B are electropherograms showing the measurements of the electroosmotic velocities to illustrate the preferred embodiment of the invention.

FIG. 3 is an electropherogram showing the measurement of the electroosmotic velocity of an electrolyte containing a micelle to illustrate the invention.

FIGS. 4, 5 are electropherograms illustrating a preferred method for determining the electroosmotic velocity.

DETAILED DESCRIPTION OF THE INVENTION

FIG. 1 is a schematic diagram of a system for determining electroosmotic velocity to illustrate the preferred embodiment of the invention. As shown in FIG. 1, system 10 includes a reservoir 12 of a first electrolyte whose electroosmotic velocity in the capillary 14 is to be determined. One end of tube 14 is immersed in reservoir 12. The other end of tube 14 is immersed in a second reservoir 16. In order to measure the electroosmotic velocity of the first electrolyte in capillary 14 and reservoir 12, the electrolyte in reservoir 16 is such that it has substantially the same chemical properties as the electrolyte in reservoir 12 but such that its resistivity is different from that of the electrolyte in reservoir 12. A high voltage is applied by a voltage supply 18 across the two reservoirs causing the second electrolyte in reservoir 16 to enter capillary tube 14 and to replace the first electrolyte present in tube 14 continuously until all of the first electrolyte in tube 14 has been replaced.

In order to measure the change in current through the electrolytes in the tube, a resistor 20 is connected in series with the two reservoirs. Therefore the change in current through the two electrolytes in the two reservoirs and in tube 14 may be recorded as a change in voltage across resistor 20 by a chart recorder 22. When the second electrolyte in reservoir 16 enters tube 14, thereby replacing a portion of the first electrolyte originally in tube 14, the resistance of the electrolyte column in tube 14 changes in resistivity since the two electrolytes have different resistivities. This causes the current flowing in the circuit through the two electrolytes to change in magnitude. For example, if the second electrolyte has a higher resistivity than the first electrolyte it replaces, the resistance of the electrolyte column in tube 14 increases after some of the first electrolyte is replaced by the second electrolyte in tube 14. Therefore, the current flowing through resistor 20 will decrease, causing a corresponding drop in voltage recorded by recorder 22. This is illustrated, for example, in the graph of FIG. 2A, where the current shown is that recorded by recorder 22 beginning at a time when tube 14 is filled by the first electrolyte in reservoir 12, before any of the electrolyte in reservoir 16 has entered tube 14. Thus, the current through resistor 20 decreases until the point when all of the first electrolyte in tube 14 has been replaced by the second electrolyte in reservoir 16. At such point, there is no further increase in the resistance of the electrolyte column in tube 14 so that the current recorded remains constant over time.

From the above, it is evident that the beginning time of the recording time t0 coincides with the point when the second electrolyte enters the tube 14 to replace the first electrolyte and time t1 coincides with the point in time when all of the first electrolyte in tube 14 has been replaced by the second electrolyte in reservoir 16. Therefore, the time difference between t0 and t1 is the time needed for all of the first electrolyte in tube 14 to be replaced by the second electrolyte. In other words, during the time interval (t1-t0), the first electrolyte has flowed through the length of the capillary tube 14. Since the length of the capillary tube 14 can be easily measured, the electroosmotic velocity of the first electrolyte is thereby determined by the ratio of the length of tube 14 to the time (t1-t0).

Since the two electrolytes have substantially the same chemical properties, they will have substantially the same effect on the inner surface of the capillary. This eliminates one possible source of error in measuring electroosmotic velocity. In the preferred embodiment, the second electrolyte may comprise the same electrolyte as that in the first electrolyte but at different concentration. In one study that has been found to be satisfactory, the first electrolyte consists of 20 mM sodium phosphate buffer with a pH of about 7.0. The second electrolyte is prepared by diluting the first electrolyte with water at a ratio of 19:1 of electrolyte to water so that the concentration of the second electrolyte is 95% that of the first electrolyte. Thus the concentrations of the two electrolytes will need to differ by only a small amount to yield a measurable difference in the currents detected through resistor 20. It is conceivable that the second electrolyte may have a composition different from that of the first electrolyte; all such variations are within the scope of the invention.

In the above example, the two electrolytes differ only in concentration of the dissolved substance. One question that arises is whether the electroosmotic velocity is a strong function of electrolyte concentration. For this purpose, reservoir 16 has been filled with a 20 mM sodium phosphate buffer and reservoir 12 as well as tube 14 are filled with 19 mM sodium phosphate buffer instead. Again the same voltage is applied by power supply 18 across the two reservoirs. The resulting current versus time plot is shown in FIG. 2B. As shown in FIG. 2B, (t3-t2) is the time required for the first electrolyte in reservoir 16 to replace entirely the second electrolyte in tube 14. It is confirmed that (t3-t2) is about the same as (t1-t0) in FIG. 2A. Hence it appears that the electroosmotic velocity is not a strong function of electrolyte concentration.

The above described system and method for measuring electroosmotic velocity of the first electrolyte described in reference to FIGS. 1, 2A may be used for deducing the electrophoretic mobility of a species, a property which characterizes such species. Thus if a sample with a number of components is introduced in the tube 14, these components will acquire positive or negative charges. Therefore, the electric field applied by supply 18 will exert a force on positively charged components to cause them to move to the negatively charged electrode and on negatively charged components to cause them to move to the positively charged electrode. Therefore the actual velocity of each of these components is the vector sum of two velocities: the velocity of the first electrolyte as a whole and the velocity of electrophoretic flow of such component. Thus if V is the actual velocity of the component, $V_{eo}$ electroosmotic velocity of the electrolyte as a whole and $V_e$ the electrophoretic velocity of the component, the actual velocity V is given by:

$$V = V_e + V_{eo}, \text{ and}$$

the electrophoretic mobility $U_e$ is given by:

$$U_e = V_e/E,$$

where E is the electric field applied by power supply 18. Therefore if the actual velocity of the component and the electroosmotic velocity are measured, the electrophoretic mobility of the component may be deduced from the above equations since the applied electric field E is a known quantity.

The actual velocity of the component may be measured by employing a detector 24 placed adjacent to tube 14 in a conventional manner. Thus if the length of the capillary tube portion through which the component in the first electrolyte must flow through in order to reach detector 24 is L, the actual velocity of the component is given by:

$$V = L/T_m$$

where $T_m$ is the time when the sample is injected into the inlet end of tube 14 until the time when detector 24 detects the component. Obviously, the electrophoretic mobility of a number of components in a sample may be measured in a similar manner in one single measurement where one or more detectors 24, resistor 20 and chart recorder 22 are all used in one single operation. If the sample is injected into the first electrolyte in tube 14 at the inlet end, and the first electrolyte together with the sample are replaced by the second electrolyte in the same manner as that described above, both the electroosmotic velocity of the first electrolyte and the actual velocities of the components of the sample may be determined in one measurement process. This is the preferred method described above in the summary of the invention.

It is possible, of course, to measure in a separate experiment the migration rates of the sample components as described above in the summary of the invention. Thus after the electroosmotic velocity of the first electrolyte has been determined as described above, the same capillary is filled with the first electrolyte. The sample is injected which is followed by more of the first electrolyte. Substantially the same voltage as that applied during the electroosmotic velocity measurement is again applied across the tube. The migration times of the sample components over a known distance are detected to determine the migration rates of the components.

As is known to those skilled in the art, micelles may be added to an electrolyte to increase the electrokinetic separation capability. Thus different components in a sample may have different affinity for the micelles. Therefore the presence of the micelles will affect the migration rate of such components. However, in order to measure accurately the migration rates of these components, it is necessary to measure the velocity of the micelles as a reference. As is known to those skilled in the art, micelles move very slowly and its velocity is difficult to detect. The system proposed by applicants provide a convenient method by which migration rate of the micelles can be readily determined. This is illustrated in reference to FIGS. 1 and 3.

In reference to FIG. 1, reservoir 12 and tube 14 are filled by a first electrolyte and reservoir 16 a second electrolyte mixed with micelles. In this illustration, the second electrolyte has a lower resistivity than the first electrolyte so that current increases when the second electrolyte and micelles replace the first electrolyte in tube 14. The micelle used may for example be sodium dodecyl sulfate; it being understood that the migration rates of other micelles may be measured in essentially the same manner.

The increase in current shown in FIG. 3 is accounted for by the presence of both sodium and dodecyl sulfate ions. The sodium ions in the second electrolyte will migrate relatively quickly, which accounts for much of the increase in current flow. As illustrated in FIG. 3, the rate of change of current changes at time t5, at which time sodium ions have reached the other end of tube 14 by time t5. After time t5, the current flow contributed by the movement of sodium ions remains constant, and any increase in current is that contributed by the dodecyl sulfate ions. The dodecyl sulfate ions, on the other hand, move very slowly along tube 14 and these ions account for a continuous but small incremental increase in current flow between time t5 and t6. At time t6, the current flow detected by recorder 22 becomes constant, showing that the dodecyl sulfate ions have finally reached the other end of tube 14 by time t6. Therefore, the time interval (t6-t4) is the migration time required for the micelle ions to move through the length of capillary tube 14. The actual velocity of components in the sample present in the electrolyte is again the vector sum of the electrophoretic migration rate and the migration rate of the micelles. The actual migration rate of the components in the presence of the micelles may be detected using detector 24 as before. The migration rate of the micelles is detected as described above in reference to FIGS. 1 and 3. Therefore the electrophoretic migration rate of the components may be determined.

In the method described above in reference to FIGS. 1 and 2A, the various currents measured at different times are recorded on a current versus time plot as data points and a line is drawn to represent current as a function of time. Where the data point deviates from the line drawn, the difference between the data point and the value of the current indicated by the graph drawn is the error term for such data point. Such error terms are minimized by conventional methods. In one conventional method, for example, the graph is drawn to minimize the error terms described above. As is evident from FIGS. 2A, 2B, the point in time at which current becomes constant is not always well defined. To increase the accuracy of measurement, data points recorded at or near the time when current becomes constant may be discarded and the graph redrawn to minimize error terms until the total error is minimized.

In the above described method in reference to FIGS. 1, 2A, in order to measure the time required for the first electrolyte to travel the whole length of tube 14, one would have to wait until the first electrolyte in tube 14 has been totally replaced by the second electrolyte. Frequently, this may take considerable time. Applicants propose an alternative preferred method which is described as follows.

Again, reservoir 10 and tube 14 are filled with the first electrolyte and reservoir 16 with the second electrolyte and power supply 18 applies a voltage across the two reservoirs causing the first electrolyte in tube 14 to be replaced by the second electrolyte in reservoir 16. Instead of having to wait until the current flow becomes constant over time, indicating that all of the first electrolyte in tube 14 has been replaced by the second electrolyte, current is measured for only a short time interval. Either before or after the above described process, tube 14 is filled by the second electrolyte and power supply 18 is used to apply the same voltage across the two ends of tube 14, causing the electrolyte to flow towards one end of the tube. The replaced second electrolyte however is replaced by the same second electrolyte so that, the current measured is constant These two measurements together enables the determination of the time required for the first electrolyte to travel the length of tube 14 as described below.

For example, tube 14 and reservoirs 12, 16 are all filled by the second electrolyte and a constant current passing through resistor 20 is I2. Then reservoir 12, 14 are filled by the first electrolyte, reservoir 16 still containing the second electrolyte, and the same voltage is applied across the two reservoirs by power supply 18 as before. The current values I1, I3 are then measured respectively at times t7, t8. The time t7 may conveniently be simply the starting point when power supply 18 first applies voltage across the two reservoirs, causing the second electrolyte in reservoir 16 to start replacing the first electrolyte in tube 14. For a short time interval t7 to t8, the current flowing through resistor 20 is sampled so that the graph 50 in straight solid line may be plotted as shown in FIG. 4. Assuming that the rate of change of current remains the same throughout the process in which the first electrolyte in tube 14 is replaced by the second electrolyte, graph 50 is simply extended as a straight line until the current value falls to the value I2, at which point all of the first electrolyte would have been replaced by the second electrolyte. The time t9 at which this happens is therefore the time at which all of the first electrolyte would have travelled through the length of tube 14. The ratio of the length of tube 14 to the time period (t9-t7) is therefore the electroosmotic velocity of the first electrolyte.

While initial time period t7 to t8 is conveniently chosen as the sampling time period, it will be understood that other sampling time periods may be chosen as well. All such variations are within the scope of the invention. Also, more than two current measurements are preferably made between t7 and t8 to provide more data points for graph 50, thereby improving its accuracy.

If reservoir 12 and tube 14 contain the second electrolyte and reservoir 16 the first electrolyte, the measurement is as illustrated in FIG. 5. The current during an initial time period t10 to t11 is sampled and the straight solid line graph 60 is plotted as shown in FIG. 5. The current through the electrolyte when tube 14 is entirely filled by the first electrolyte is also measured and is of value I1. Therefore, graph 60 can be again extended until it intersects the straight line graph representing current equals I1 so that the total time required for the first electrolyte to enter and replace the second electrolyte throughout the length of tube 14 is (t12-t10). Therefore, the electroosmotic velocity of the first electrolyte is given by the ratio of the length of the tube L to (t12-t10). Again, a different sampling time period may be used instead of t10 to t11.

The above preferred method has the advantage that much less time is required to determine the electroosmotic velocity. Current need to be sampled only for a short time period such as between time t7 and t8 or between t10 and t11. The constant current value (I2 in FIG. 4 and I1 in FIG. 5) can be measured simply and quickly.

The invention has been described by reference to particular implementations and embodiments. It will be understood that various modifications and changes may be made without departing from the invention whose scope was to be limited only by the appended claims.

Included as part of the specification is the article "Current-Monitoring Method for Measuring the electroosmotic flow rate in capillary zone Electrophoresis" by Huang, Gordon and Zare, *Analytical Chemistry*, 1988, 60, 1837–1838. The article is attached hereto as Appendix A.

APPENDIX A: Page 1 of 2

Current-Monitoring Method for Measuring the Electroosmotic Flow Rate in Capillary Zone Electrophoresis Xiaohua Huang, Manuel J. Gordon, and Richard N. Zare*

*Department of Chemistry, Stanford University, Stanford, California 94305*

Capillary zone electrophoresis (CZE) is attracting much attention (1-4) as a new separation technique that can complement high-performance liquid chromatography (HPLC). In CZE a migration channel of capillary dimensions is filled with electrolyte; a sample to be analyzed is injected at one end of the channel; and a high voltage is applied across the channel. When the electrolyte contacts the walls of the capillary, the inner surface of the capillary becomes charged, either through the ionization of surface groups on the capillary walls or through the adsorption of charged species from the electrolyte onto the inner surface. In either case, the electrolyte inside the capillary is no longer electroneutral but acquires a net charge, which may be positive or negative. Under the action of the applied electric field, the electrolyte moves toward one end of the capillary, and this movement is referred to as electroosmotic (electroendosmotic) flow. In addition to the bulk flow of the electrolyte, electrophoresis also takes place; that is, the applied electric field exerts a force on positively charged species to cause them to move to the negatively charged electrode and on negatively charged species to cause them to move to the positively charged electrode. As a result, the components in the injected sample separate into distinct zones, based on their different mobilities. However, in many cases, the rate of electrophoretic flow is typically less than the rate of electroosmotic flow. Consequently, species in the injected sample move in one direction—the direction of the electroosmotic flow—and thus the different species can be detected as each zone passes through some suitable detector located downstream from the capillary inlet.

Clearly, a precise characterization of the electroosmotic flow is highly desirable not only for understanding CZE but also for optimizing the operation of CZE in analyzing a given sample. One way to measure the electroosmotic flow rate is to record the elution time of an injected uncharged marker solute, which will be carried through the capillary under the action of only electroosmotic flow (4-6). For this purpose it is necessary that the marker solute be truly neutral, that it have negligible interaction with the capillary walls, and that it be readily detected. Another way is to weigh the mass of electrolyte transferred from the capillary inlet to the capillary outlet over a timed interval (7). For this purpose, losses caused by evaporation must be eliminated and the use of a digital balance appears to be recommended. Both of these procedures have been demonstrated to give reliable measurements of the electroosmotic flow rate, provided that some care is taken. We describe here what we believe might be a simpler procedure for measuring the electroosmotic flow rate. It is based on recording the time history of the current during CZE operation. Thus the new method requires no special type of injected solute or detector, and it can be used by anyone carrying out CZE separations.

EXPERIMENTAL SECTION

Figure 1 shows the experimental setup used for measuring the electroosmotic flow rate by monitoring the current in the CZE system. The polarity of the power supply is chosen so that the electroosmotic flow is from electrolyte reservoir 1 to electrolyte reservoir 2 through the capillary tube T. The procedure is to fill capillary tube T and reservoir 2 with electrolyte at a concentration $C$ and to fill reservoir 1 with the same electrolyte but at a different concentration $C'$. As the electrolyte at concentration $C'$ in reservoir 1 migrates into capillary tube T during CZE, it displaces an equal volume of electrolyte at concentration $C$ in the tubing. As a consequence, the total resistance of the fluid in the capillary tube changes, and this change can be followed by recording the current $I$ during the CZE operation. A resistor, R (metal film, 10.0 k$\Omega$, 2W), is inserted between the reservoir 2 electrode and ground. The choice of 10.0 k$\Omega$ for this resistor means that a 1-$\mu$A current change would produce a 10-mV potential drop across the resistor. A chart recorder (Linear, Model 585) is connected directly across the resistor R. In this manner $I$ is recorded as a function of time during the CZE operation. The concentrations $C$ and $C'$ need not differ greatly for the electroosmotic flow rate to be measured. As will be shown below, it is sufficient for $C$ and $C'$ to differ by about 5%.

In our studies we used an electrolyte consisting of 20 mM sodium phosphate buffer with a pH of about 7.0. This solution is said to have the concentration $C$. The same electrolyte mixture at concentration $C'$ is prepared by diluting the electrolyte at concentration $C$ with water (19:1) so that $C' = 0.95C$.

The bipolar power supply delivers 19-21 kV, and the untreated fused silica capillary (Scientific Glass Engineering, Austin, TX) has an inside diameter of 75 $\mu$m and is 63 cm long. Under these conditions, with the current $I$ at about 40 $\mu$A, the electroosmotic flow is in the direction indicated in Figure 1 when the polarity of the power supply is positive.

RESULTS AND DISCUSSION

Figure 2, trace a, presents the CZE current $I$ as a function of time when reservoir 1 has phosphate buffer at concentration $C'$ and capillary tube T and reservoir 2 have phosphate buffer at concentration $C$ (where $C' = 0.95C$). Note that the current falls with time as the electrolyte of concentration $C'$ displaces continuously the electrolyte of concentration $C$ in the capillary tube. This current drop continues until the entire capillary becomes filled with electrolyte of concentration $C'$. If the direction of electroosmotic flow is reversed from what is shown in Figure 1, then there would be no current change. Hence this experimental setup readily determines the direction of electroosmotic flow. The time interval $\Delta t$ is the time required to complete the filling of capillary tube T by the electroosmotic flow of the electrolyte in reservoir 1 into the tube. Thus with a knowledge of the capillary length $L$ between reservoirs 1 and 2, the electroosmotic flow rate, $v_{eo}$, is given by $L/\Delta t$.

Because two different concentrations of the same electrolyte were employed in the above measurement, the question arises whether the electroosmotic flow rate is a strong function of electrolyte concentration, and if so, what does our measured value of $v_{eo}$ mean. To investigate this question, we reversed the procedure; namely, we filled reservoir 1 with phosphate buffer at concentration $C$ and capillary tube T and reservoir 2 with phosphate buffer at concentration $C'$. The resulting current versus time plot is presented in trace c of Figure 2. We observe no significant difference between the values of $\Delta t$ for trace a and trace c. An unpaired comparison $t$ test was applied to two groups of runs resulting in $t = 0.833$, which shows that the differences are not statistically significant. Therefore we conclude that the electroosmotic flow rate can be accurately determined by this simple current measurement method.

As a further check on this conclusion, we used an on-column conductivity detector (8) to measure the electroosmotic flow rate by observing the conductivity change as a function of time. The results are shown in traces b and d of Figure 2. The

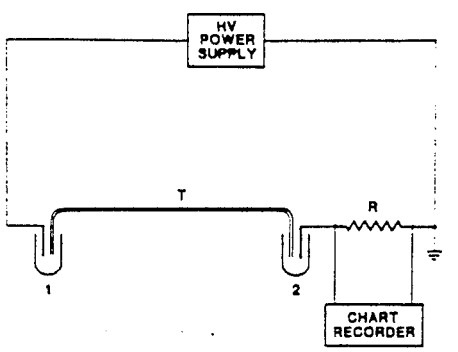

Figure 1. Schematic diagram of the current measurement for determining the electroosmotic flow rate. Here 1 and 2 denote electrolyte reservoirs, which are connected by the capillary tube T.

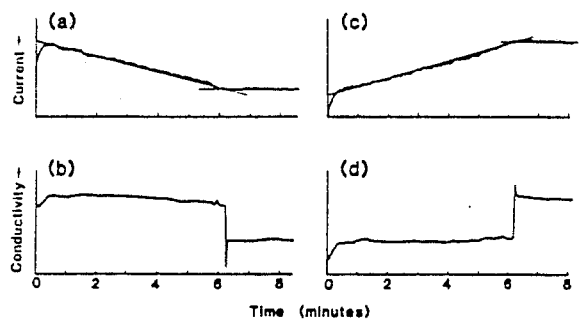

Figure 2. Electropherograms showing the measurement of the electroosmotic flow rate. Trace a shows the CZE current versus time for 19 mM phosphate buffer replacing 20 mM phosphate buffer in the capillary tube, and trace b shows, under the same conditions, the conductivity change. Traces c and d are the corresponding electropherograms when 20 mM phosphate buffer replaces 19 mM phosphate buffer in the capillary tube. The actual operating conditions are given in the text. In traces a and c regression lines are indicated to aid identification of the slope change.

conductivity detector is located only 5 mm from the outlet so that the distance to the detector is almost the same as the total length of the capillary tube, i.e., $l \approx L$. Consequently, the conductivity change should take place at almost the same time the slope in the current changes. This is observed to hold by comparing in Figure 2 trace a to trace b and trace c to trace d.

We claim:

1. A method for determining the electrokinetic properties of an electrolyte in an electrokinetic separation by means of an elongated capillary tube having an inlet end and an outlet end, said method comprising:
   introducing a first electrolyte into the tube at its inlet end;
   introducing a second electrolyte into the capillary tube at its inlet end, wherein said second electrolyte has an electrical resistivity which differs from that of the first electrolyte but substantially the same chemical properties as the first electrolyte;
   applying a voltage to and current through the electrolyte to cause electroosmotic flow of the electrolytes towards the outlet end and to cause the second electrolyte to replace the first electrolyte continuously;
   measuring the current through the electrolytes as a function of time; and
   determining the electroosmotic velocity of the first or second electrolyte.

We also compared the current-monitoring method with the neutral marker method (4–6) for determining the electroosmotic flow rate. Following Tsuda, Nomura, and Nakagawa (9), we used pyridine as the neutral marker, and we employed a UV absorption detector. Three different experiments were carried out at an electric field strength of 300 V/cm in a capillary tube of 75-μm i.d. and 70-cm length (50 cm to the detector). First we filled reservoir 1, capillary tube T, and reservoir 2 with the same concentration of phosphate buffer (20 mM). By measuring the time of appearance of the UV absorption peak corresponding to pyridine and by knowing the length of the capillary to the UV absorption detector, we determined the electroosmotic flow rate to be $v_{eo} = 0.14943 \pm 0.001763$ cm/s where the uncertainty is one standard deviation (eight runs). The second and third experiments are for the same concentration conditions as in traces a and c of Figure 2, respectively. In the second experiment, we find $v_{eo} = 0.15006 \pm 0.001198$ cm/s for the neutral marker method and $v_{eo} = 0.014904 \pm 0.002655$ cm/s for the current-monitoring method. In the third experiment, the corresponding values are $v_{eo} = 0.14972 \pm 0.001279$ and $v_{eo} = 0.014861 \pm 0.002468$ cm/s, respectively. We used a paired $t$ test to determine if these measurements have a systematic relationship. We found for the second experiment $t = 1.184$ and for the third experiment $t = 1.033$. These values of $t$ indicate that there is no significant difference between these two methods. The current-monitoring method is generally applicable and often more convenient. We recommend its use.

LITERATURE CITED (1) Cohen, A. S.; Terabe, S.; Smith, J. A.; Karger, B. L. *Anal. Chem.* 1987, *59*, 1021.
(2) Hjertén, S.; Elenbring, K.; Kilár, F.; Liao, J-L.; Chen, A. J. C.; Siebert, C. J.; Zhu, M-D. *J. Chromatogr.* 1987, *403*, 47.
(3) Jorgenson, J. W.; Lukacs, K. D. *Science (Washington, D.C.)* 1983, *222*, 266.
(4) Tsuda, T.; Nakagawa, G.; Sato, M.; Yagi, K. *J. Appl. Biochem.* 1983, *5*, 330.
(5) Lauer, H. H.; McManigill, D. *Anal. Chem.* 1986, *58*, 166.
(6) Walbroehl, Y.; Jorgenson, J. W. *Anal. Chem.* 1986, *58*, 479.
(7) Altria, K. D.; Simpson, C. F. *Anal. Proc. (London)* 1986, *23*, 453.
(8) Huang, X.; Pang, T-K. J.; Gordon, M. J.; Zare, R. N. *Anal. Chem.* 1987, *59*, 2747.
(9) Tsuda, T.; Nomura, K.; Nakagawa, G. *J. Chromatogr.* 1982, *248*, 241.

RECEIVED for review February 2, 1988. Accepted May 9, 1988. Support for this work by Beckman Instruments, Inc., is gratefully acknowledged.

2. The method of claim 1, further comprising:
   performing a process to determine migration rate of a component of a sample in one or both electrolytes; and
   calculating the electrophoretic mobility of the component.

3. The method of claim 2, wherein said process to determine migration rate comprises steps to be performed separately from the remaining steps of the method, wherein said steps of the migration rate determining process comprise:
   introducing the first electrolyte into the inlet end of the capillary tube;
   injecting a sample into the inlet end of the tube;
   introducing more of the first electrolyte into the inlet end of the tube after the sample has been injected to replace the first electrolyte and sample previously introduced into the tube;
   applying the voltage to and current through the electrolytes to cause electroosmotic flow of the electrolytes towards the outlet end, to cause the laterintroduced first electrolyte to replace the sample and earlier-introduced first electrolyte continuously, and to cause the component of the sample to migrate toward the outlet end; and measuring the migration rate of the component of the sample.

4. The method of claim 3, wherein the step of measuring the migration rate of the component includes measuring a time interval required for the component to migrate over a known distance.

5. The method of claim 2, wherein said process to determine migration rate comprises steps to be performed together with the remaining steps of the method, wherein said steps of the migration rate determining process comprise:

injecting a sample into the inlet end of the tube after the first electrolyte has been introduced but before the second electrolyte is introduced;

wherein the voltage applied also causes the second electrolyte to replace the sample as well as the first electrolyte continuously, and causes a component of the sample to migrate toward the outlet end; and measuring the migration rate of the component of the sample.

6. The method of claim 5, wherein the step of measuring the migration rate of the component includes measuring a time interval required for the component to migrate over a known distance.

7. The method of claim 1, wherein the current through the electrolytes is measured as a function of time for a time period less than that required for the first electrolyte in the tube to be entirely replaced by the second electrolyte, said method further comprising:

filling the tube with the second electrolyte;
applying the voltage across the tube; and
measuring the current through the second electrolyte.

8. An apparatus for determining the electrokinetic properties of an electrolyte in an electrokinetic separation, said apparatus comprising:

an elongated capillary tube having an inlet end and an outlet end suitable for holding electrolytes;

a first electrolyte;

a second electrolyte suitable to be introduced into the capillary tube at the inlet end after the first electrolyte has been introduced, wherein said second electrolyte has an electrical resistivity which differs from that of the first electrolyte but substantially the same chemical properties as the first electrolyte;

means for applying a voltage to and current through the electrolytes to cause electroosmotic flow of the electrolytes towards the outlet end and to cause the second electrolyte to replace the first electrolyte in the tube continuously;

means for measuring the current through the electrolytes as a function of time; and means for determining the electroosmotic velocity of the first or second electrolyte.

9. The apparatus of claim 8, wherein said tube is suitable for holding a sample composed of one or more components, said apparatus further comprising means for measuring the velocity of a component in the sample.

10. The apparatus of claim 8, wherein said second electrolyte includes micelles.

11. The apparatus of claim 8, wherein said first electrolyte comprises a first buffer including two compounds, and wherein said second electrolyte comprises a second buffer including the same two compounds, where the proportion between the two compounds in the second buffer is different from that of the first buffer.

12. A method for determining the electrokinetic properties of an electrolyte in an electrokinetic separation by means of an elongated capillary tube having an inlet end and an outlet end, said method comprising:

introducing a plurality of electrolytes into the tube at its inlet end, wherein said plurality of electrolytes are introduced one after another one electrolyte at a time, wherein said plurality of electrolytes have different electrical resistivities but substantially the same chemical properties;

applying a voltage to and current through the electrolytes to cause electroosmotic flow of the electrolytes towards the outlet end and to cause at least one of said plurality of electrolytes to be replaced by another electrolyte continuously;

measuring the current through the electrolytes as a function of time; and determining the electroosmotic velocity of at least one of said plurality of electrolytes.

13. An apparatus for determining the electrokinetic properties of electrolytes in an electrokinetic separation, said apparatus comprising:

an elongated capillary tube having an inlet end and an outlet end suitable for holding electrolytes;

a plurality of electrolytes suitable to be introduced into the tube at its inlet end one after another and one electrolyte at a time, wherein said plurality of electrolytes have different electrical resistivities but substantially the same chemical properties;

means for applying a voltage to and current through the electrolytes after they have been introduced into the tube to cause electroosmotic flow of the electrolyte towards the outlet end and to cause at least one of said plurality of electrolytes to be replaced by another electrolyte continuously;

means for measuring the current through the electrolytes as a function of time; and means for determining the electroosmotic velocity of at least one of the plurality of electrolytes.

* * * * *